(12) United States Patent
Ramirez

(10) Patent No.: US 10,274,412 B2
(45) Date of Patent: Apr. 30, 2019

(54) FLOW CYTOMETRY DATA SEGMENTATION RESULT EVALUATION SYSTEMS AND METHODS

(71) Applicant: Beckman Coulter, Inc., Brea, CA (US)

(72) Inventor: Carlos Ramirez, Miami, FL (US)

(73) Assignee: BECKMAN COULTER, INC., Brea, CA (US)

(*) Notice: Subject to any disclaimer, the term of this patent is extended or adjusted under 35 U.S.C. 154(b) by 646 days.

(21) Appl. No.: 14/443,263

(22) PCT Filed: Nov. 15, 2013

(86) PCT No.: PCT/US2013/070432
§ 371 (c)(1),
(2) Date: May 15, 2015

(87) PCT Pub. No.: WO2014/078741
PCT Pub. Date: May 22, 2014

(65) Prior Publication Data
US 2015/0330888 A1 Nov. 19, 2015

Related U.S. Application Data

(60) Provisional application No. 61/727,474, filed on Nov. 16, 2012.

(51) Int. Cl.
*G01N 15/14* (2006.01)
*G06T 7/00* (2017.01)
(Continued)

(52) U.S. Cl.
CPC ..... *G01N 15/1429* (2013.01); *G01N 15/1459* (2013.01); *G06K 9/6226* (2013.01);
(Continued)

(58) Field of Classification Search
CPC .......... G01N 15/1429; G01N 15/1459; G01N 2015/1402; G01N 2015/1477; G01N 2015/1488; G06K 9/6226
See application file for complete search history.

(56) References Cited

U.S. PATENT DOCUMENTS 8,548,219 B2 * 10/2013 Ortyn ................... G01N 15/147
356/326
2003/0078703 A1 4/2003 Potts et al.
(Continued)

FOREIGN PATENT DOCUMENTS

WO 9305478 A1 3/1993
WO 0185914 A2 11/2001

OTHER PUBLICATIONS

Bashanti, A., et al. "A Survey of Flow Cytometry Data Analysis Methods", Advances in Bioinformatics, vol. 2009, Article ID 584603, Accepted Aug. 22, 2009, 20 pages.
(Continued)

*Primary Examiner* — Elias Desta
(74) *Attorney, Agent, or Firm* — Kilpatrick Townsend & Stockton, LLP

(57) ABSTRACT

Systems and methods evaluate the results produced by histogram segmenting techniques. Exemplary techniques assess boundary region decision or placement techniques according to histogram based metrics, population based metrics, or combinations or transformations thereof.

23 Claims, 11 Drawing Sheets

(51) Int. Cl.
*G06K 9/62* (2006.01)
*G06T 7/12* (2017.01)
*G06T 7/143* (2017.01)
*G06T 7/194* (2017.01)
*G06T 7/136* (2017.01)

(52) U.S. Cl.
CPC .............. *G06T 7/0002* (2013.01); *G06T 7/12* (2017.01); *G06T 7/136* (2017.01); *G06T 7/143* (2017.01); *G06T 7/194* (2017.01); *G01N 2015/1402* (2013.01); *G01N 2015/1477* (2013.01); *G01N 2015/1488* (2013.01); *G06T 2207/30004* (2013.01); *G06T 2207/30168* (2013.01)

(56) References Cited

U.S. PATENT DOCUMENTS

2007/0237227 A1* 10/2007 Yang .................. H04N 17/004
375/240.12

2010/0111400 A1 5/2010 Ramirez et al.
2012/0245889 A1 9/2012 Zhu et al.

OTHER PUBLICATIONS

Thairu, A., "Quality control and analysis of flow cytometry data", Jun. 1, 2012, Retrieved on Feb. 14, 2014 from http://www2.math.su.se/matstat/reports/master/2012/rep6/report.pdf, 39 pages.

Liu, L., et al. "Comparing and Clustering Flow Cytometry Data", Bioinformatics and Biomedicine, 2008, BIBM 2008, IEEE International Conference on IEEE, Piscataway, NJ, USA, Nov. 3, 2008, pp. 305-309.

Finak, et al., "Qualifier: An automated pipeline for quality assessment of gated flow cytometry data", BMC Bioinformatics, BiodMed Central, London, GB, vol. 13, No. 1, Sep. 28, 2012, 15 pages.

Jegatha, D. L., et al. "A Survey on Internal Validity Measure for Cluster Validation", International Journal of Computer Science and Engineering Survey, vol. 1, No. 2, Nov. 29, 2010, pp. 85-102.

International Search Report and Written Opinion of related PCT/US2013/070432, dated Feb. 24, 2014.

* cited by examiner

HISTOGRAM BASED METRIC
DATA DISTRIBUTION (2 OF 2)

(COMPARING FIGS.3A AND 3B, UNIMODAL)

(COMPARING FIGS.4A AND 4B, MULTIMODAL)

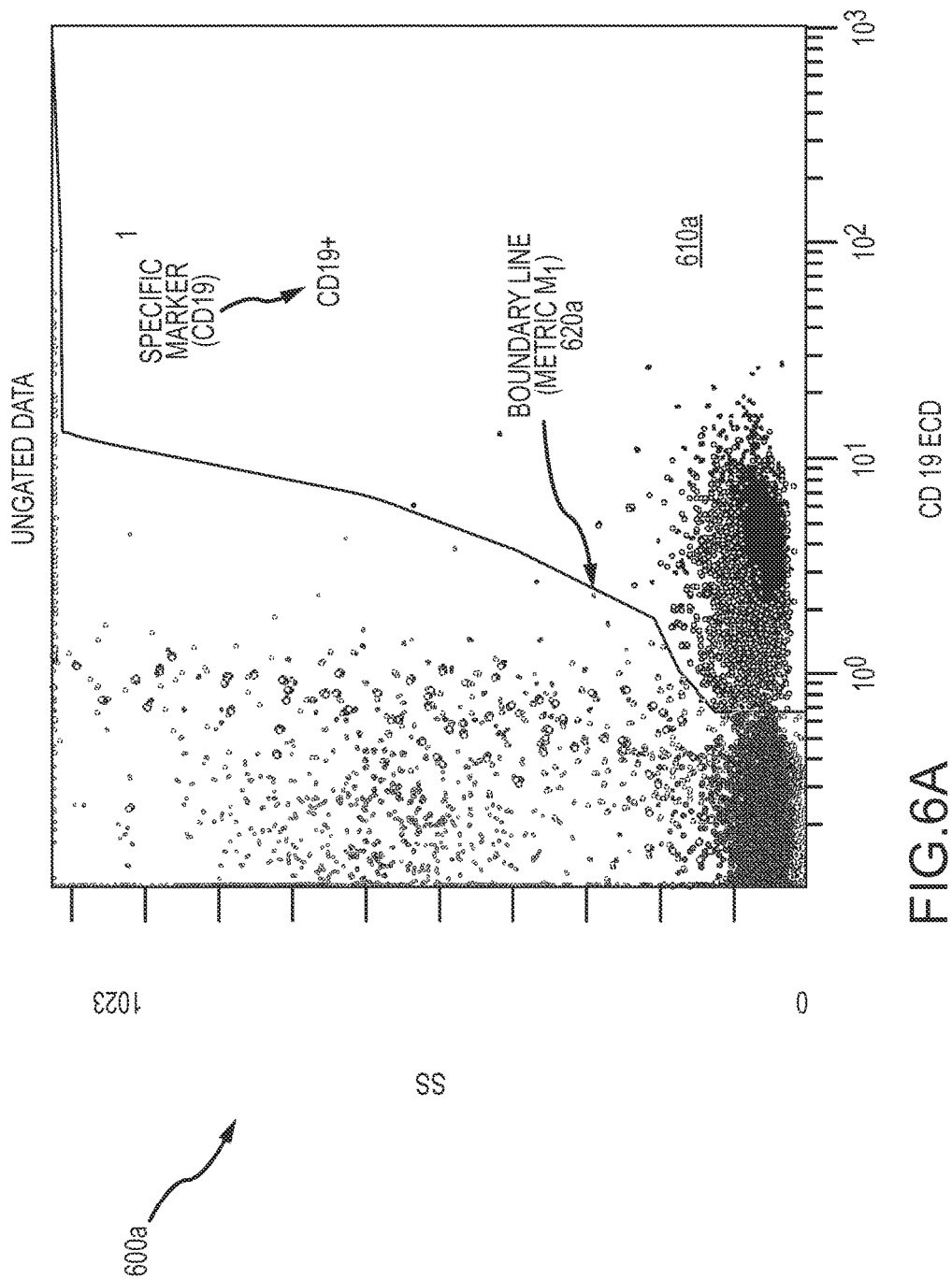

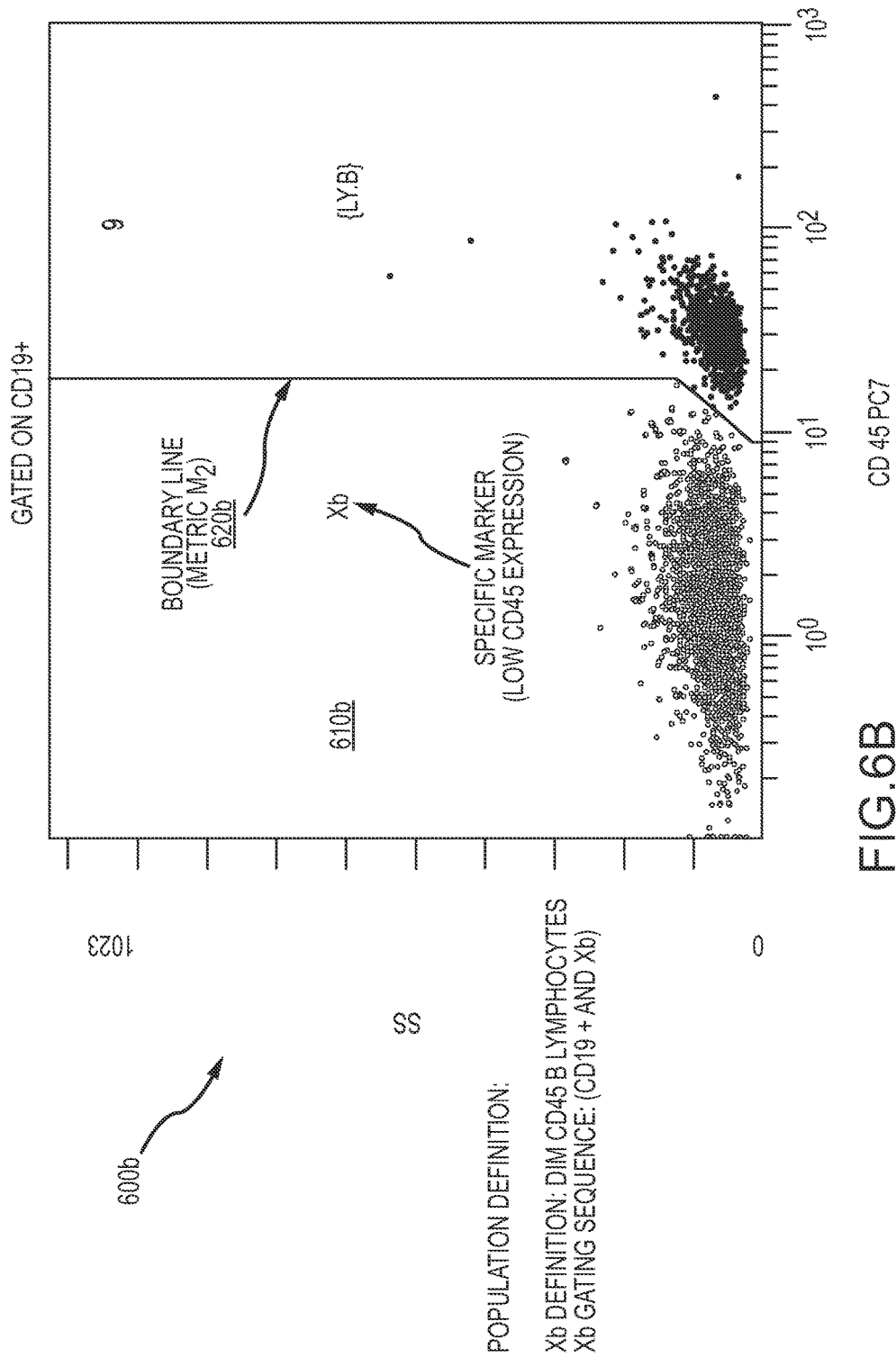

POPULATION BASED METRIC

Xb POPULATION METRIC:

$$\boxed{Xb\ POPULATION\ SCORE} = MINIMUM(M_1, M_2, M'_3)$$

700

METRICS:
$M_1$ = CD19+ REGION SEPARABILITY METRIC
$M_2$ = Xb REGION SEPARABILITY METRIC
$M_3$ = Xb DATA DISTRIBUTION SCORE (COMPARED TO A NORMALIZED GAUSSIAN CURVE)
$M_4$ = Xb PERCENTAGE
$M_5$ = Xb NUMBER OF EVENTS $$M'_3 = M_3 + ((100 - M_3) \times (1 - P_S))$$

$$P_S = MINIMUM\left(\frac{M_4}{0.8}, \frac{M_5}{100}\right)$$

FIG.7

FLOW CYTOMETRY DATA SEGMENTATION RESULT EVALUATION SYSTEMS AND METHODS

CROSS-REFERENCES TO RELATED APPLICATIONS

This application is a 35 U.S.C. § 371 U.S. National Stage Entry of International Application Serial No. PCT/US2013/070432 (WO 2014/078741 A1) filed Nov. 15, 2013, which claims the benefit of U.S. Provisional Patent Application No. 61/727,474 filed Nov. 16, 2012. The entire content of each of the above filings is incorporated herein by reference.

BACKGROUND OF THE INVENTION

Embodiments of the present invention relate to flow cytometry, and in particular to systems and methods for assessing the quality of results obtained by boundary placement techniques.

Flow cytometry immunophenotyping of hematopoietic disorders is a complex and demanding task that requires a good understanding of cell lineages, developmental pathways, and physiological changes, as well as broad experience in hematopathology.

Flow cytometry allows simultaneous multiparametric analysis of thousands of particles per second by suspending cells in a stream of fluid and passing them by an electronic detection apparatus. The data generated can be plotted into histograms and divided into regions. Regions are shapes that are drawn or positioned around a population of interest on a one or two parameter histogram. Exemplary region shapes include two dimensional polygons, circles, ellipses, irregular shapes, or the like. Individual events exemplified in the data correspond to unique combinations of parameters, and are accumulated in cases where multiple instances of such combinations are present. When a region is used to limit or isolate cells or events that are drawn or positioned on a histogram, such that those isolated cells or events can be manifested in a subsequent histogram, this process is referred to as gating. The data accumulated into histograms can be separated or clustered based on fluorescence intensity, in a series of sequential steps known as "gating" involving one or more regions. In some cases, gates are combined with each other using Boolean logic (AND, OR, NOT). A common technique involves using gates sequentially. In some cases, gates are performed in parallel.

In the last decade, advances in instrumentation and reagent technologies have enabled simultaneous single-cell measurement of tens of surface and intracellular markers, as well as tens of signaling molecules, positioning flow cytometry to play an ever increasing role in medicine and systems biology.

However, the rapid expansion of flow cytometry applications has outpaced the functionality of traditional analysis tools used to interpret flow cytometry data such that scientists are faced with the daunting prospect of manually identifying interesting cell populations in 20 dimensional data from a collection of millions of cells.

The Beckman Coulter tetraCXP system software, stemCXP and CytoDiff CXP software are nonlimiting examples of automated flow cytometry solutions. They provide a gating algorithm to separate populations of interest in the multidimensional space and report percentages and other clinical parameters to the user. Automated identification of homogenous cell populations that share a particular function is referred to as automated gating. These solutions alleviate the need for high expertise and reduce the processing time required for manually gating flow cytometry data. Additional benefits include labor cost reductions, uniformity in the analysis, and reduction of user induced errors.

A 2005 study involving 15 institutions (H. T. Maecker, A. Rinfret, P. D'Souza, et al., "Standardization of cytokine flow cytometry assays," BMC Immunology, vol. 6, article 13, 2005) showed that the mean interlaboratory coefficient of variation ranged from 17-44%, even though the same samples and reagents were used and the preparation of samples was standardized. Even though all analyses were conducted by individuals with expertise in flow cytometry, most of the variation was attributed to gating.

Hence, although flow cytometry assay technologies provide real benefits to the field of hematology, still further advances and improvements are desirable. Embodiments of the present invention provide solutions to at least some of these outstanding needs.

BRIEF SUMMARY OF THE INVENTION

Embodiments of the present invention encompass systems and methods for informing flow cytometry users about the validity of results produced by automated histogram gating techniques. Often, certain metrics are used to evaluate the gating techniques. Hence, where automated histogram gating produces compromised results as part of a flow cytometry protocol, embodiments of the present invention provide metric-based mechanisms to inform the user of such cases.

In this way, benefits of automation are preserved or enhanced, by giving the user information about whether the validity of the test results are reliable or not. As nonlimiting examples, questionable results are caused by hardware malfunctions, incorrect settings, improper sample preparation, excessive sample aging, highly abnormal cases, or the like.

Where questionable results are observed, the samples may typically require careful review by the laboratory staff in order to decide an appropriate course of action. As a component of automating such review techniques, embodiments of the present invention encompass techniques that provide metrics which are used as input to decision rules to support the decision making process involved in the validation of flow cytometry results.

Some embodiments of the present invention encompass systems and methods for calculating metrics that are used in conjunction with other parameters to assess the quality of the results of a single or multiple tube flow cytometry analysis. In some cases, the metrics are used as input to decision rules for enhancing the review process of problematic samples in an automated system.

According to some embodiments, a metric refers to a numerical value bounded between a lower limit (e.g. 0) and an upper limit (e.g. 100). In certain embodiments, a numerical value at or close to the lower bound is associated to a low level or complete absence of the feature described by the metric. Conversely, a numerical value at or close to the upper bound is associated with a high level or full presence of the feature in some embodiments.

Some embodiments of the present invention also encompass systems and methods for transforming raw metrics by using information about the significance of the metric. In some cases, the significance is determined based on features related to the data used to calculate the metric.

In one aspect, embodiments of the present invention encompass systems and methods for assessing the quality of a boundary used for isolating a subset of events from a set of accumulated events, where the subset corresponds to a population of interest sharing a physical property and the set corresponds to sample particles. Exemplary methods of assessing the boundary quality include obtaining a plot of the set of accumulated events, where the set of accumulated events includes the subset of events, and isolating, with the boundary, the subset of events from other events of the set of accumulated events. Further, methods include determining a quality assessment metric for the boundary. In some cases, the plot includes a histogram. In some cases, placement of the boundary is automated. In some cases, placement of the boundary is performed manually. In some cases, the quality assessment metric is based on a distance between the subset of events and the boundary. In some cases, the quality assessment metric is based on a distance between the subset of events and a characteristic point. In some cases, the characteristic point comprises a member selected from the group consisting of a mean of the subset and a mode of the subset. According to some embodiments, the quality assessment metric can be based on a number of events falling on the boundary. In some instances, the boundary at least partially defines a region corresponding to the population of interest. According to some embodiments, the quality assessment metric can be based on a comparison between a statistical parameter calculated for the subset and a theoretical distribution. In some cases, the statistical parameter is a mean or a standard deviation. In some cases, the theoretical distribution is a Gaussian distribution. According to some embodiments, the comparison is based on a similarity measure characterizing the statistical parameter and the theoretical distribution, where the similarity measure is calculated based on a sum of paired event distances or a correlation coefficient. According to some embodiments, boundary quality assessment techniques can include determining a population based metric, where the population based metric is a function of a combination of multiple independent metrics. The combination of multiple independent metrics can include a first independent metric and a second independent metric. In some cases, the first independent metric includes the quality assessment metric. In some cases, the function includes an aggregation operator. In some cases, the aggregation operator can be an average, a minimum, or a maximum. In some cases, the first independent metric is based on a number of events falling on the boundary and the second independent metric is based on a comparison between a statistical parameter calculated for the subset and a theoretical distribution. In some cases, the first independent metric corresponds to the population of interest, and the second independent metric corresponds to another population of interest.

In another aspect, embodiments of the present invention encompass systems and methods for assessing the quality of a data segmentation technique. Exemplary methods of assessing the quality of a data segmentation technique may include obtaining data for a set of accumulated events, where the set of accumulated events corresponds to sample particles, and segmenting, using the data segmentation technique, data for a subset of the set of accumulated events, where the subset corresponds to a population of interest, and where the segmenting step produces a data segmentation result. Methods can also include determining the quality of the data segmentation technique based on the data segmentation result.

In yet another aspect, embodiments of the present invention encompass flow cytometers that can include, for example, an electronic detection apparatus configured to generate data for sample particles, where the data corresponds to a set of accumulated events, and where the set of accumulated events includes a subset of events corresponding to a population of interest sharing a physical property. Flow cytometers can also include a display configured to display a plot of the set of accumulated events and a boundary that isolates the subset of events from other events of the set of accumulated events. Flow cytometers can also include a processor, and a control logic executed by the processor to determine a quality assessment metric for the boundary.

In one aspect, embodiments of the present invention encompass a method for characterizing a sub-population of particles in a sample, each particle in the sub-population sharing a common property. Exemplary methods can comprise obtaining a set of data points, each data point representative of the presence or absence of one or more selected properties of a particle in the sample, plotting the set of data points on a graphical display, drawing a boundary around a group of data points on the graphical display, the boundary estimated to separate the data points corresponding to the sub-population of particles sharing said common property from the data points corresponding to other particles in the sample, and determining a reliability metric for the boundary.

Embodiments of the present invention encompass a method, wherein the boundary is calculated automatically based on a distribution of the data points.

Embodiments of the present invention encompass a method, wherein the boundary is drawn based on a manual input of a user.

Embodiments of the present invention encompass a method, wherein the reliability metric is based on a distance between the boundary and one or more of the data points.

Embodiments of the present invention encompass a method, wherein the reliability metric is based on a distance between the boundary and a statistical value representative of a distribution of the data points separated by the boundary.

Embodiments of the present invention encompass a method, wherein the statistical value is one of a mean, a median, a mode, and a centroid (i.e. a geometric center of a cluster).

Embodiments of the present invention encompass a method, wherein the distance between the boundary and the statistical value is compared to a value representing a spread of the distribution of data points.

Embodiments of the present invention encompass a method, wherein the value representing the spread of the distribution is a standard deviation.

Embodiments of the present invention encompass a method, wherein the reliability metric is based on a comparison of a distribution of the data points separated by the boundary with a theoretical distribution.

Embodiments of the present invention encompass a method, wherein the theoretical distribution is a Gaussian distribution.

Embodiments of the present invention encompass a method, wherein the comparison is based on a correlation coefficient between the distribution of data points and the theoretical distribution.

Embodiments of the present invention encompass a method, wherein the comparison is based on a sum of paired distances between the distribution of data points and the theoretical distribution.

Embodiments of the present invention encompass a method, wherein the reliability metric is based on a comparison of a distribution of the data points separated by the boundary with a reference distribution.

Embodiments of the present invention encompass a method, wherein the reference distribution is a distribution of data points from a prior sample.

Embodiments of the present invention encompass a method, wherein the prior sample is a control sample. The control sample can be a sample containing a known concentration of particles sharing the common property.

Embodiments of the present invention encompass a method, wherein the reliability metric is a measure of how closely the estimated boundary matches an ideal boundary.

Embodiments of the present invention encompass a method, wherein the ideal boundary separates all data points corresponding to particles actually having the common property from data points corresponding to particles actually not having the common property.

Embodiments of the present invention encompass a method, wherein a low determined value for the reliability metric is indicative of a bad sample or an instrument malfunction.

Embodiments of the present invention encompass a method comprising providing a warning of the bad sample or the instrument malfunction if the determined value for the reliability metric is low.

Embodiments of the present invention encompass a method, wherein a low determined value for the reliability metric is indicative of an improperly drawn boundary.

Embodiments of the present invention encompass a method comprising applying a transformation function to the reliability metric to provide a weighted metric.

Embodiments of the present invention encompass a method, wherein the transformation function includes a population significance factor.

Embodiments of the present invention encompass a method, wherein the population significance factor is a function of a set of n features.

Embodiments of the present invention encompass a method, wherein the function of the set of n features includes an aggregation operator combining the n features.

Embodiments of the present invention encompass a method, wherein the aggregation operator is one of the average, the minimum, and the maximum of values of the n features.

Embodiments of the present invention encompass a method comprising drawing a second boundary to further divide the set of data points, and determining a second reliability metric for the second boundary.

Embodiments of the present invention encompass a method, wherein the second boundary divides the data points corresponding to the sub-population of particles sharing said common property.

Embodiments of the present invention encompass a method comprising determining a composite reliability metric for the combination of first and second reliability metrics.

Embodiments of the present invention encompass a method, wherein the first and second reliability metrics are combined using an aggregation operator.

Embodiments of the present invention encompass a method, wherein the aggregation operator is a minimum value among the first and second reliability metrics.

Embodiments of the present invention encompass a method comprising determining a threshold value for the reliability metric.

Embodiments of the present invention encompass a method comprising providing a warning if the reliability metric is at or below the threshold value.

Embodiments of the present invention encompass a method comprising providing a warning if the reliability metric exceeds the threshold value.

Embodiments of the present invention encompass a method, wherein the set of data points are measurements made by a flow cytometer.

In one aspect, embodiments of the present invention encompass a method for characterizing particles in a sample. The method comprises measuring a value for each of the particles with a flow cytometer, the value indicative of the presence or absence of a property of the particle, plotting the values on a graphical display, estimating a border that separates the plotted values of particles having the property from the plotted values of other particles in the sample, and determining a reliability metric for the estimated border. Related methods may include any of the aspects described herein.

In one aspect, embodiments of the present invention encompass a flow cytometer comprising a detector configured to measure a value for each of a plurality particles in a sample, the measured value representative of a property of the particle, a graphical display configured to plot the measured values and to draw a border enclosing a group of the measured values corresponding to a putative sub-population of particles sharing a common property, and a processor configured to determine a reliability metric for the drawn border. Exemplary flow cytometers may be used according to any of the method aspects described herein.

In still another aspect, embodiments of the present invention encompass systems and methods for evaluating an automated flow cytometry gate. Exemplary methods can include obtaining a histogram based metric for the gate, and evaluating the automated gate based on the histogram based metric. In other aspects, exemplary methods may include obtaining a population based metric for the gate, and evaluating the automated gate based on the population based metric. In another aspect, embodiments of the present invention encompass systems and methods for transforming a raw metric into a weighted metric. Exemplary methods can include obtaining the raw metric, obtaining a significance measure corresponding to data from which the raw metric is obtained, and transforming the raw metric into the weighted metric based on the significance measure.

BRIEF DESCRIPTION OF THE DRAWINGS

FIGS. 6A and 6B depict aspects of data segmentation techniques, according to embodiments of the present invention.

FIG. 7 depicts aspects of population metric techniques, according to embodiments of the present invention.

DETAILED DESCRIPTION OF THE INVENTION

Figure 1:
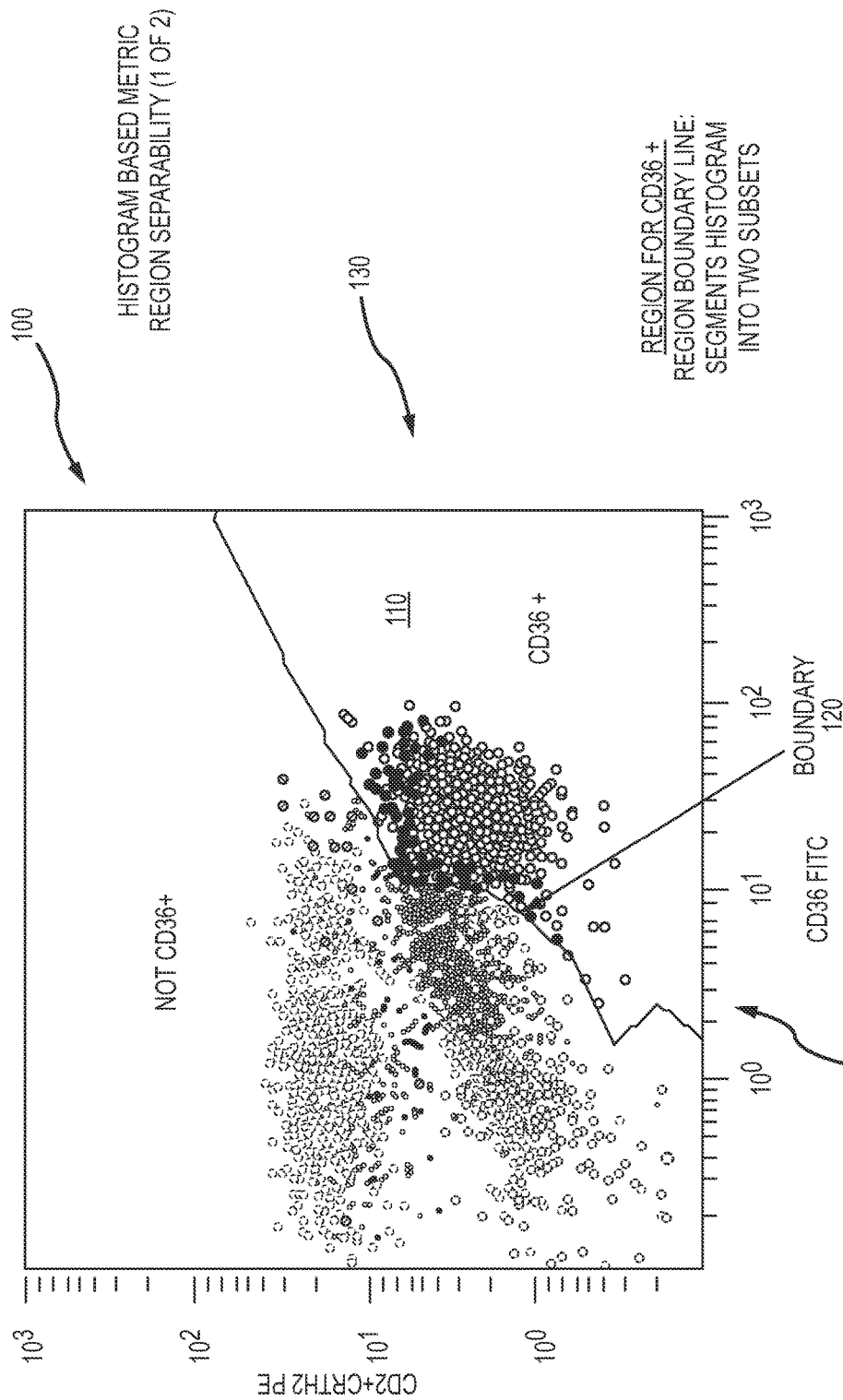
FIG. 1 illustrates aspects of a region separability histogram based metric technique, according to embodiments of the present invention.

Embodiments of the present invention generally relate to systems and methods of particle analysis and grouping. More particularly, embodiments of the present invention relate to systems and methods for evaluating or assessing the quality of segmentation techniques that are used to classify particles, for example where two dimensional histograms are created from data relating to physical properties of the particles.

Particle analyzers, such as hematology analyzers or flow cytometers, can process biological samples for particle analysis. They can measure physical properties of biological particles in biological samples for analysis. Exemplary physical property measurements include electro-optical measurements. The measured physical properties can be viewed as a multidimensional space. Each dimension in the multidimensional space can correspond to a measured physical property. Particles sharing similar physical properties can group into clusters in the multidimensional space. Each can cluster correspond to a specific particle population. Due to the statistical distribution of the particles and the multiple dimensions involved, the process of identifying such clusters by an automated method or algorithm is often a complex task.

Some embodiments of the present invention encompass a variety of metrics for use in assessing the quality of automated segmenting algorithm results as well as manual segmenting results. For example, flow cytometry often involves techniques for separating data into different segments. Embodiments of the present invention include approaches for evaluating or assessing the quality of the results of such segmentation techniques. The metric techniques disclosed herein can be divided into two categories, so as to include histogram based metrics and population based metrics. According to some embodiments, histogram based metrics are computed based on features that are extracted on an individual one-dimensional or multidimensional histogram that has been segmented by one or more regions.

According to some embodiments, population based metrics can be created for each of the populations of interest being targeted by the flow cytometry panel. In some embodiments population based metrics are based on the gating sequence followed to isolate the population of interest, histogram based metrics and their statistical significance, as well as aggregation operators to produce a numerical value.

In a nonlimiting example, a method of assessing the quality of a data segmentation technique may include obtaining data for a set of accumulated events, and using a data segmentation technique to segment data for a subset of the accumulated events. The set can correspond to sample particles such as biological particles in a blood sample, and the subset can correspond to a population of interest. The segmenting step can produce a data segmentation result, and methods can include determining the quality of the data segmentation technique based on the data segmentation result.

Two Histogram Based Metrics: Region Separability and Data Distribution

Histogram based metrics are typically based on features extracted from a single histogram. Some embodiments of the present invention encompass two histogram based metrics, specifically a region separability score and a data distribution score. The region separability score is used in some embodiments to analyze the data along the boundary of a region, whereas the data distribution score is used in certain embodiments to analyze the behavior of the data within the region.

In some embodiments these metrics are used effectively in instances where events at each side of a histogram region boundary line are not of similar proportionality in some cases, or otherwise present predefined data distribution patterns. As a nonlimiting example, in some embodiments such metrics account for a region boundary line that isolates a small population, or where more than one population is involved in creating a multimodal distribution at either side of the boundary line.

Region Separability Metric ($1^{st}$ Histogram Based Metric of 2)

In some embodiments the region separability metric is used to assess the goodness of separation achieved by an automated or nonautomated (e.g. manually performed) method, as a nonlimiting example when isolating data events that fall into a particular section of the histogram by means of a region boundary line. Exemplary manual, automated, and other gating, boundary decision, region placement, or histogram segmentation techniques which can be evaluated by embodiments of the present invention are discussed by Bashashati et al. in "A Survey of Flow Cytometry Data Analysis Methods", Advances in Bioinformatics, Volume 2009, Article ID 584603, the content of which is incorporated herein by reference, as well as in in US Patent Publication No. 2010/01111400 which is also incorporated herein by reference.

As a nonlimiting example, a region boundary line with a high goodness of separation minimizes the distance of all events inside the region to a characteristic point (i.e., mean, mode or any other parameter) while maximizing their distance to the region boundary line. Hence, in some embodiments a region boundary line with a high goodness of separation corresponds to the lowest histogram density path separating the events to be isolated. Exemplary region boundary line separability metrics are used in certain embodiments to obtain improved separation in flow cytometry applications, and relatedly are used in certain embodiments to provide improved region boundary line placement.

Turning now to the drawings, FIG. 1 illustrates aspects of a region separability histogram based metric technique, according to embodiments of the present invention. As shown in the 2D histogram 100 here (which in some embodiments originates from gated events or in certain embodiments originates from ungated events), a region 110 named CD36+ and its corresponding boundary line 120 divides the histogram 100 into two separate sets of events. The CD36+ region 110 is defined by the boundary line 120, in combination with the outer limits of the histogram boundaries (maximum CD36 FITC value on the right side 130, minimum CD2+ CRTH2 PE value on the lower side 140). The CD36+ region separates the histogram into two independent sets of data. The original data shown include all events, and the region separates the events into two separate sets, such that a first set 110 is inside of the region (CD36+) 110 and a second set is outside of the region (NOT CD36+). Hence, the region is a shape that separates the data into two subsets.

To obtain the region separability metric, as characterized by Equation 1, the number of gated events falling on the region boundary line (i.e. lines defining the polygon region) are counted. As a nonlimiting example, in some embodiments this involves determining the number of events falling on the boundary line 120 which defines the CD36+ region.

Further, the total number of events being analyzed is obtained. In some embodiments this number refers to a predefined subset of all collected events. As a nonlimiting example, in certain embodiments the total number of events being analyzed refers to the number of white blood cells after separation from red cell debris.

Figure 2:
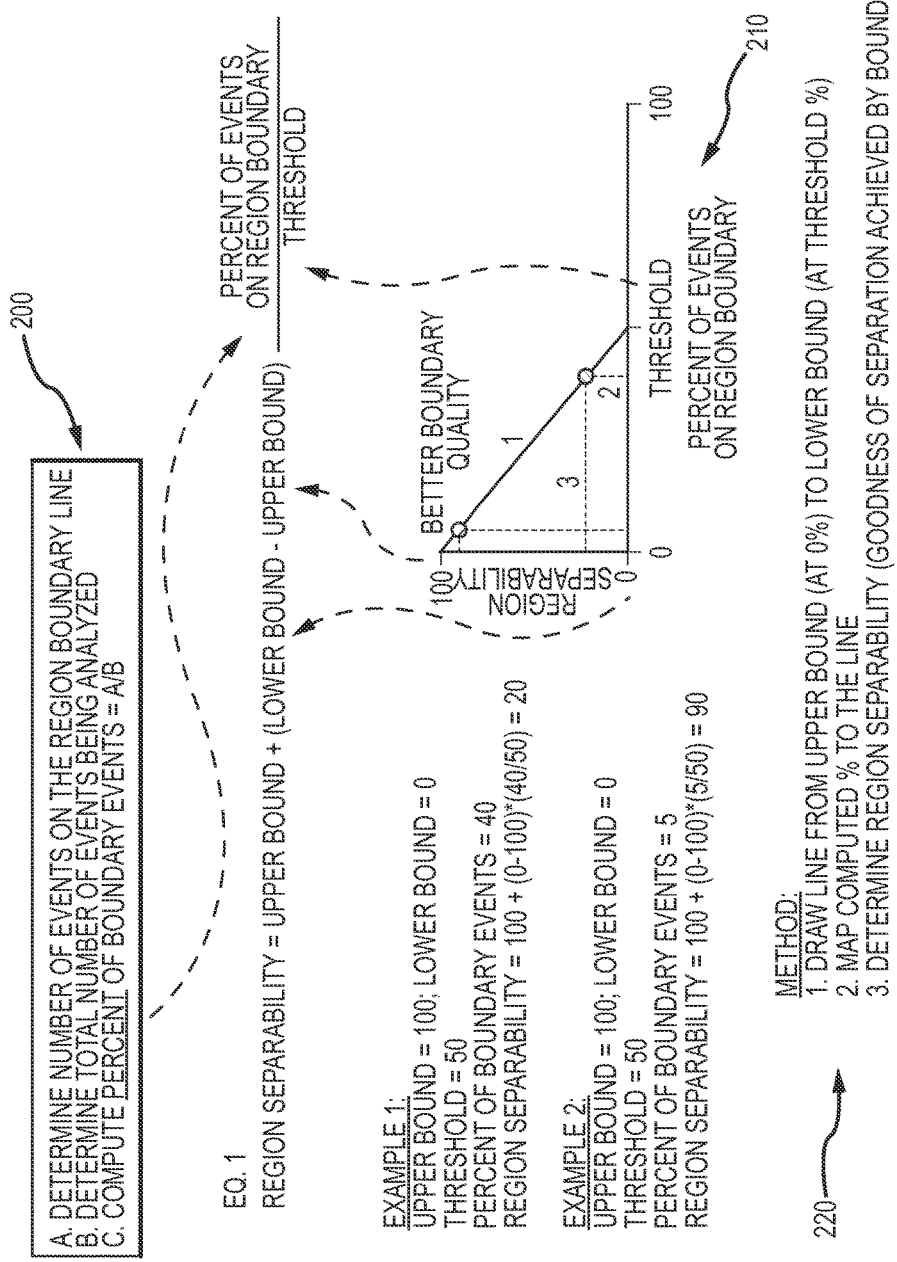
FIG. 2 depicts aspects of techniques for determining a region separability metric, according to embodiments of the present invention.

As depicted in FIG. 2, in some embodiments the percent of events on the region boundary is then calculated by a method 200 that includes dividing the number of events on the region boundary line (Step A) by the total number of events being analyzed (Step B). In certain embodiments the percent of boundary events computed (Step C) is then divided by a threshold value, as indicated in Equation 1.

This equation operates to transform the percentage of boundary events into a numerical value between, as a nonlimiting example, a lower bound (e.g. 0) and an upper bound (e.g. 100) by comparing the percentage to a certain threshold.

As illustrated in the region separability metric calculation graph 210 and corresponding method 220 shown in FIG. 2, a line is drawn between the upper bound (e.g. 100) at 0 percent and the lower bound (e.g. 0) at the threshold percent (Step 1). This line corresponds to a linearly decreasing value extending between the two end points. If the computed percentage (x-axis) falls between 0 percent and the predefined threshold percent, then the computed percentage is mapped to the line (Step 2), and then to the region separability metric score (Step 3). In the embodiment shown here as a nonlimiting example, a numerical value of 100 for the region separability metric corresponds to zero events at the same location as the region boundary, whereas a numerical value 0 for the region separability metric is reported once the computed percentage equals or exceeds the threshold percentage.

The region separability metric correlates the number of events on the boundary line(s) of the region with the certainty related to the region boundary line placement. Hence, the lower the computed percentage with respect to a predefined threshold limit percentage, the more certainty there is on the goodness of the segmentation achieved by the region (e.g. Example 2). Conversely, the higher the computed percentage with respect to a predefined threshold limit percentage, the less certainty there is on the goodness of the segmentation achieved by the region (e.g. Example 1).

Selection of the predefined limit or threshold percentage allows the customization of the region separability metric to different population sizes and known clinical significance of the population being considered. In some embodiments the threshold is also made dynamic so as to change according to the size of the population being isolated.

In some instances, a region separability metric involves a Fisher distance or any other approach that measures the degree of separation between two data distributions. In some cases, a region separability metric involves a cluster validity measure.

Data Distribution Metric ($2^{nd}$ Histogram Based Metric of 2)

A data distribution metric is used in some embodiments to quantify the similarity of a population data distribution to a known theoretical distribution. Hence, in certain embodiments a data distribution metric is particularly useful to detect if a segmented population comes from a well-defined process or if the population is a subset of another population, a random process (noise), or some combination of the above. Some embodiments of the present invention encompass data distribution metrics which maintain a low computational load, and which in certain embodiments are used to compare the similarity of two data distributions.

Figure 3A:
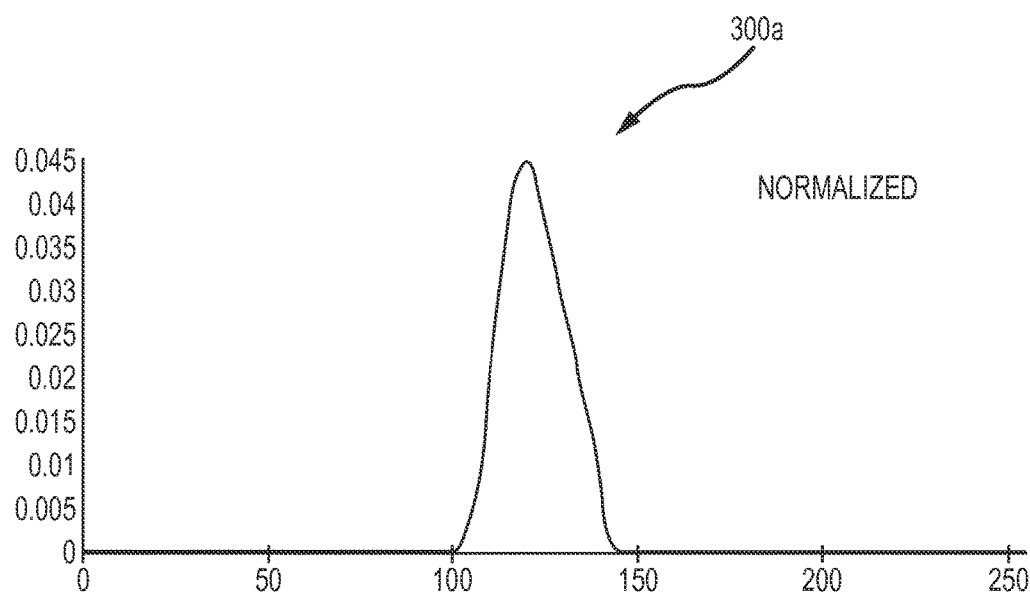
FIG. 3A depicts aspects of a unimodal bell-shaped sample data distribution after normalization.
Figure 3B:
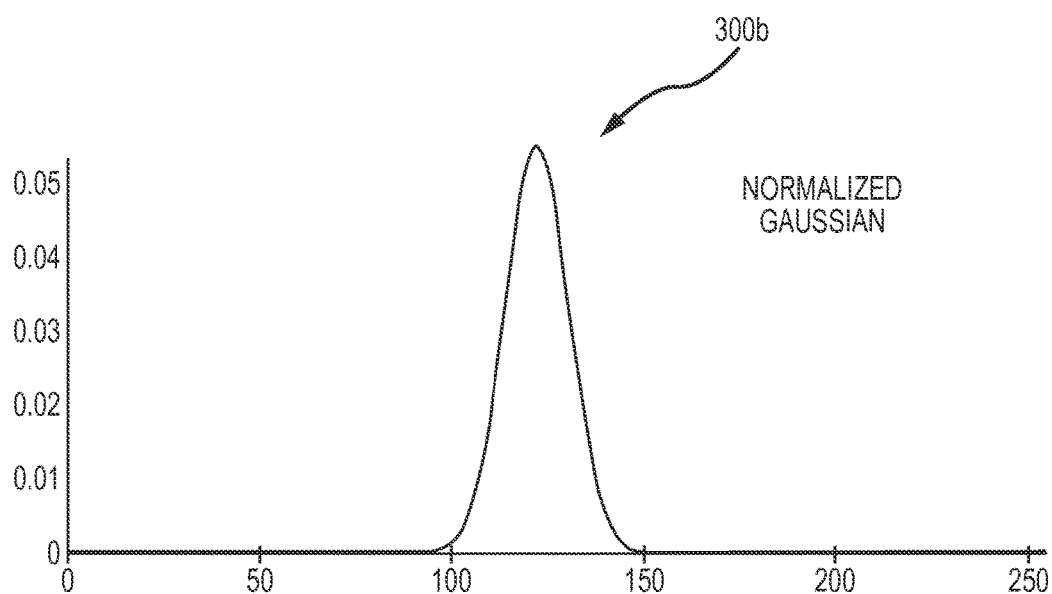
FIG. 3B depicts aspects of a normalized Gaussian curve for the distribution of FIG. 3A, according to embodiments of the present invention.

FIG. 3A depicts a nonlimiting example of a unimodal bell-shaped sample data distribution 300a after normalization, and FIG. 3B depicts a normalized Gaussian curve 300b for the distribution of FIG. 3A. Similarly, FIG. 4A depicts a nonlimiting example of a multimodal biased sample data distribution 400a after normalization, and FIG. 4B depicts a normalized Gaussian curve 400b for the distribution of FIG. 4A.

Figure 4A:
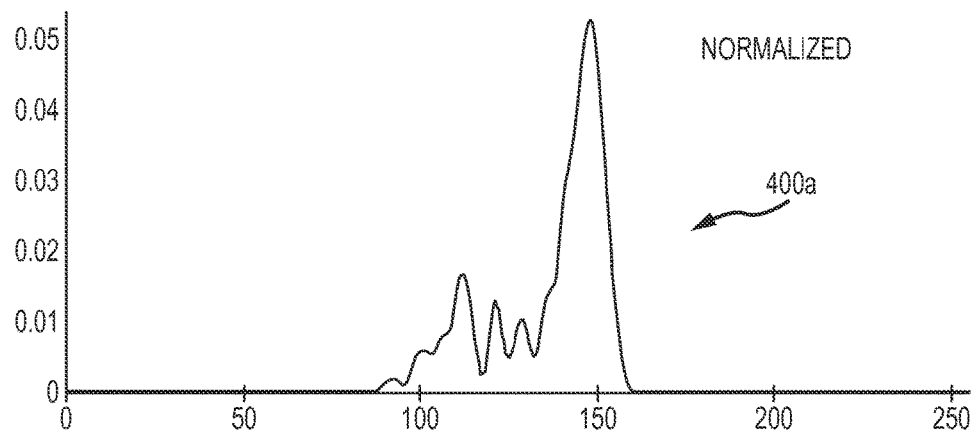
FIG. 4A depicts aspects of a multimodal biased sample data distribution after normalization.

With regard to FIGS. 3A and 4A, the value in the x-axis corresponds to the bin number of the accumulated histogram for a particular marker (e.g. CD45, CD36). In some embodiments, the histogram is accumulated with gated data and in certain embodiments the histogram is accumulated with ungated data. Related, the y-axis values are from the data itself accumulated as histogram. Hence, the units in the y-axis correspond to the total number of events (e.g. cells) at the corresponding bin associated to a particular marker (e.g. CD45) value. As shown here, histogram is normalized. That is, each y-axis value is divided by the area of the histogram such that the new area of the accumulated histograms is summed to a value of 1. In this way, the curves of FIGS. 3A and 4A are compared in some embodiments to the curves of FIGS. 3B and 4B, respectively, where the area also adds up to 1.

Figure 4B:
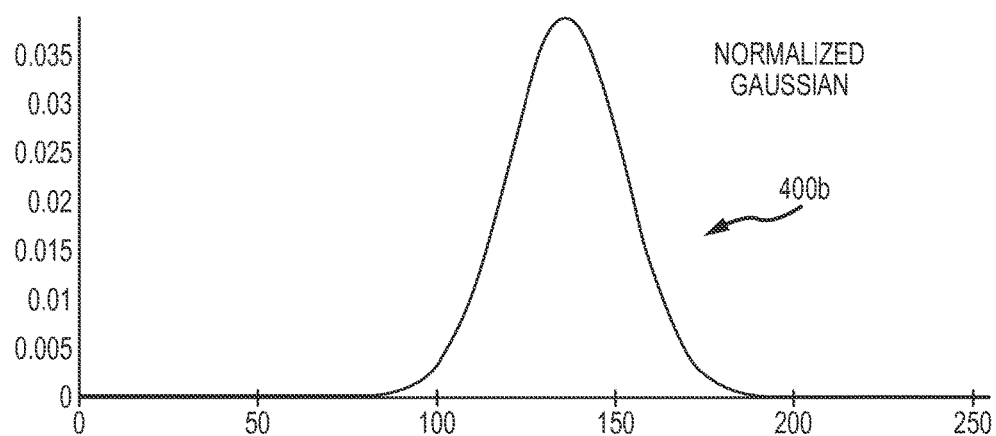
FIG. 4B depicts aspects of a normalized Gaussian curve for the distribution of FIG. 4A, according to embodiments of the present invention.

For FIGS. 3B and 4B, the x-axis and y-axis values are obtained in some embodiments by calculating the mean (mu) and standard deviation (sigma) of the data in FIGS. 3A and 4A, and applying the following equation:

$$\text{Normalized Gaussian Curve} = \frac{e^{\left[-\frac{(x-\mu)^2}{2\sigma^2}\right]}}{\sigma\sqrt{2\pi}}$$

Hence, means and standard deviations are computed for both data distributions, and normalized Gaussian curves for each distribution are generated and presented in FIGS. 3B and 4B.

Figure 5A:
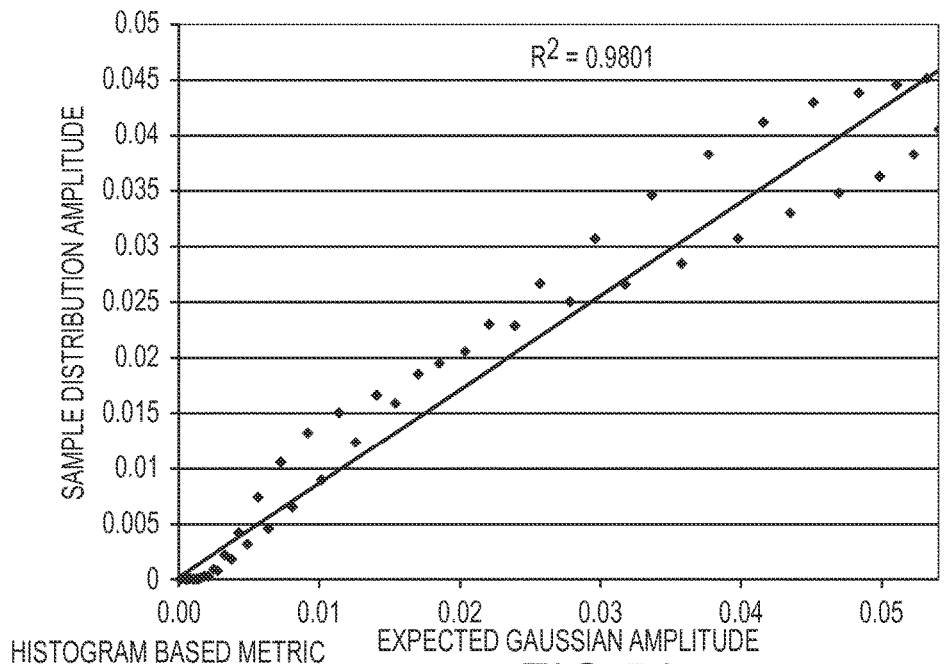
FIG. 5A depicts a comparison of sample data to theoretical data, according to embodiments of the present invention.
Figure 5B:
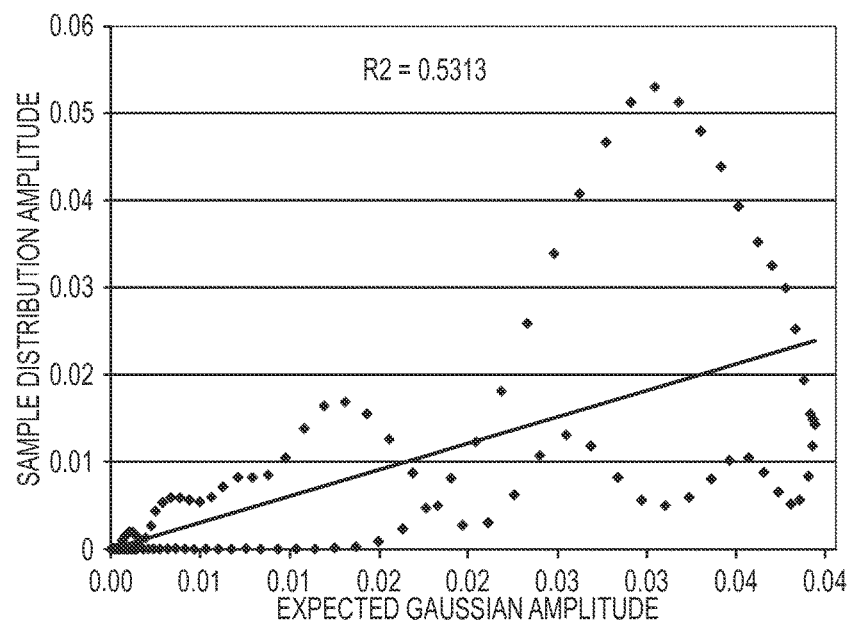
FIG. 5B depicts a comparison of sample data to theoretical data, according to embodiments of the present invention.

As shown in FIG. 5A, the sample data of FIG. 3A is in some embodiments compared to the theoretical data of FIG. 3B. Similarly, as shown in FIG. 5B, the sample data of FIG. 4A is compared in certain embodiments to the theoretical data of FIG. 4B.

In some embodiments, a data distribution score is obtained for each distribution by computing the correlation coefficient ($R^2$) between the sample data (e.g. FIGS. 3A and 4A) and the theoretical model data (e.g. FIGS. 3B and 4B), respectively. Here, the correlation coefficient or data distribution score is 0.9801 for unimodal distribution and 0.5313 for the multimodal distribution.

Accordingly, the data distribution score provides an indication of the similarity of each sample data distribution to a normalized Gaussian curve that is known for being unimodal and bell-shaped. In some embodiments this result is combined when multiple parameters are analyzed by applying an aggregation operator such as average or minimum.

In more general terms, given a set of multidimensional events labeled as belonging to the same population, parameters such as mean, standard deviation, and others is calculated for selected dimensions in some embodiments. Based on the sample statistics, in certain embodiments an ideal theoretical distribution is constructed using a predefined model. In some embodiments the theoretical model is compared against the sample distribution by calculating a similarity measure. The similarity measure is calculated in some embodiments by a variety of approaches such as sum of paired event distances, absolute errors, correlation coefficient, or the like. In certain embodiments data distribution score is calculated in the selected multidimensional space or to simplify calculation in some embodiments it is calculated for each dimension and then each individual result is combined into a final one using an aggregation operator.

According to some embodiments, a data distribution metric is based on a normality test approach, which in some embodiments involves a Shapiro-Wilk method, a Kolmogorov-Smirnov method, a Lilliefors method, an Anderson-Darling method, a D'Agostino-K squared method, a Chen-Shapiro method, or the like. In some instances, a data distribution metric is based on a graphical tool such as, as a nonlimiting example, a quantile-quantile (QQ) plot.

Population Based Metrics

In some embodiments, a population based metric provides a higher layer of information by combining independent metrics (directly or indirectly related to a particular population) into a single numerical value. In flow cytometry, in certain embodiments, a population is isolated when one or more gates are combined with each other using Boolean logic (AND, OR, NOT).

Histogram based metrics for each of the gates involved in the identification of the population are combined in some embodiments to take into account the interdependency among all gates to accurately identify the corresponding population cluster in the multidimensional space. In this way, inferences regarding the goodness of each gating step are accumulated as multiple sequential gating steps are performed. In addition, in certain embodiments other metrics specific to the population under consideration are also incorporated in the population based metric.

According to some embodiments of the present invention, an aggregation operator such as the minimum value among all independent metrics is used to combine the metrics. In some cases, another function that appropriately combines the independent metrics is applied for this purpose.

Population based metrics are used in some embodiments to summarize all the information collected by independent metrics and reduce the complexity of the sample reviewing process.

Metric Transformation

In some instances, metrics are qualified or weighted in order to control their impact in the process of reviewing sample results by the laboratory. As a nonlimiting example, a laboratory flow process is slowed down due to an unnecessary review of a sample with a low data distribution score on a particular population. The review is in some cases unnecessary because such a metric was derived from a very low absolute number of data points, or from a very low number of data points relative to the total number acquired, which makes the metric irrelevant and not trustable.

The following method describes an approach to transform a metric M into a weighted metric M' by applying a function $f(M,P_s)$ as defined below:

$$M'=f(M,P_s)$$

The function $f(M,P_s)$ corresponds to a model that is capable of modifying the metric based on the significance of the population associated to the metric. According to some embodiments, a model that drives the metric to its maximum value once the population significance is zero is implemented. The maximum value in this case is desired because it avoids unnecessary post-analysis of that particular sample from the reviewer. The model leaves the original metric unchanged when the population significance is set to 1; meaning that full trust is given to the original metric value.

$$f(M,P_S)=M+(\alpha\times(\beta-M)\times(1-P_s))$$

The parameter $\alpha$ corresponds to a weight factor to control the rate of change of M. The parameter $\beta$ is the maximum metric value (e.g. 100). The Population Significance ($P_S$) factor is in some embodiments defined as the relative importance of the population in terms of percentage, number of events, or any other statistic. In addition, a qualitative heuristic assessment is in certain embodiments also part of $P_S$ by using a number representing some a priori information about the role of this metric in the review process. In general, $P_S$ can be defined as any function that produces a value between 0 and 1 given a W set of n features, as follows:

$$P_S=f(W)$$

$$0 \leq f(W) \leq 1$$

In some embodiments definitions of $f(W)$ include any model that combines features W in a meaningful way such as, as nonlimiting examples: average, minimum, maximum, or any other suitable aggregation operator. Selection of the minimum represents a more cautious approach, whereas selection of maximum represents a less cautious approach. According to some embodiments, the function $f$ is chosen to be the minimum value among all features, as follows:

$$f(W)=\text{minimum}(w_1,w_2,\ldots,w_n)$$

As mentioned above, in some embodiments features W are related to the statistics of the population such as, as nonlimiting examples: percentage, number of events, or any other measurable feature. In addition, qualitative features such as a priori knowledge about the relative importance of the population in the overall review process in some embodiments is part of W. According to some embodiments, two features (percentage and number of events) are used to assess the population significance.

In some embodiments the percentage and number of events features are transformed into $w_1$ and $w_2$ by using mapping functions based on predefined thresholds, as follows:

$$w_1 = \text{minimum}\left(1, \frac{P_\%}{T_\%}\right)$$

$$w_2 = \text{minimum}\left(1, \frac{P_\#}{T_\#}\right)$$

Here, $P_\%$=Population percentage, $P_\#$=Population number of events, $T_\%$=Population percentage significance threshold, and I. $T_\#$=Population number of events significance threshold.

According to some embodiments, once the percentage (or number of events) exceeds the threshold, the ratio will be greater than one. Hence, in some cases, the limit to the minimum is set to one, so that where the percentage or number of events exceeds the threshold, the returned value will be the minimum of the two values, which is one (and not the ratio). According to some embodiments, it is possible to control the impact of a particular metric by setting up a threshold to a set of features, and by not reporting and/or not using the metric if the threshold is not met.

In some instances where features are close to the thresholds, issues with repeatability are possible. That is, as a nonlimiting example, consecutive runs of the same patient produce highly different results because one particular feature was barely above the threshold for one run and not for the next run. Some embodiments of the present invention avoid such inconsistency between runs by providing a smooth transition between zero "trust" to full "trust" in the metric. In a nonlimiting example, the value of $P_\%/T_\%$ is between zero (no trust) and one (full trust), and the value of $P\#/T\#$ is between zero (no trust) and one (full trust). In addition, certain embodiments of the present invention provide a framework to combine different features into a single weighting factor.

FIGS. 6A, 6B, and 7 depict aspects of a nonlimiting example where the minimum aggregation operator is applied to calculate a population based metric for the Xb population (Lymphocyte B cells with low CD45 expression).

As shown in the ungated histogram 600a of FIG. 6A, after events are accumulated in a SS versus CD19 histogram a first region 610a labeled CD19+ is applied to define or segment a subset of events associated with the CD19 marker, and a region separability metric $M_1$ is calculated for the boundary 620a of the region 610a. The term ungated as used here means, as a nonlimiting example, that the histogram 600a is built using all of the data available which was obtained by the instrument.

As shown in the gated histogram 600b of FIG. 6B, as a nonlimiting example, the subset of events gated by the CD19+ are accumulated in a SS versus CD45 histogram, a second region 610b labeled Xb is applied to define or segment the Xb population (lymphocyte B cells with low CD45 expression), and a region separability metric $M_2$ is calculated for the second region boundary 620b.

Hence, in some embodiments the first region 610a (CD19+) is used to limit or isolate cells or events that are drawn or positioned on the histogram 600a of FIG. 6A, such that those isolated cells or events are manifested in the subsequent histogram 600b of FIG. 6B. In this way, the use of the region 610a (CD19+) operates as a gating step, by limiting the number of cells from the first histogram 600a that are subsequently manifested in the second histogram 600b. As a nonlimiting example, the region 610a acts as a gate to filter out or isolate those events within the region boundaries, so that the events are extracted and placed in the next histogram. The term gated as used here means, as a nonlimiting example, that the data present in the histogram is derived using a gating step, as applied to a previous histogram.

In these embodiments, FIG. 6A depicts ungated data, and FIG. 6B depicts gated data (i.e. gated on CD19+ events). Accordingly, region boundary lines are placed on ungated data as in FIG. 6A, or on gated data as in FIG. 6B. In many cases, the parameters of a subsequent histogram are different from those used for the previous histogram. In some cases, a population is isolated using a single gating step. In some cases, a population is isolated using multiple gating steps. As discussed elsewhere here, Boolean logic is in some situations applied to histogram data. Hence, the Xb population is in some embodiments defined by CD19+ AND Xb, and the LY.B population is in some embodiments defined by CD19+ AND NOT Xb. As a nonlimiting example, methods are used to identify a particular subset of data within a larger set of data. The quality of the result obtained in FIG. 6B is dependent on the quality of the gating step that was performed on the data of the histogram of FIG. 6A. Hence, if the region boundary line is not properly placed in FIG. 6A, the data present in FIG. 6B will be deficient.

In one embodiment, the segmented results are displayed on a display such as a monitor, a projector screen, or the like. In another embodiment, the segmented results are stored on a storage device such as a hard disk, a floppy disk, a flash drive, or the like.

FIG. 7 shows that additional metrics are calculated in some embodiments, including an Xb data distribution score ($M_3$), an Xb percentage ($M_4$), and an Xb number of events ($M_5$).

As mentioned above, a function $f$ is chosen in some embodiments to be the minimum value among various features, such as $f(W)=\text{minimum}(w_1, w_2, \ldots, w_n)$. Hence, as shown in FIG. 7, the Xb population score or function 700 in certain embodiments is equal to the lowest value of the $M_1$, $M_2$, and $M'_3$ metrics. In this example, $T_\%$ and $T_\#$ have been assigned values of 0.8 and 100, respectively, meaning that full trust will be attributed to the data distribution metric $M_3$ when the Xb population percentage exceeds 0.8% and 100 events. Values for the percentage or number of events which are below their respective threshold will, in some embodiments, correspond to lower levels of trust (e.g. in a linear or monotonically decreasing fashion, for at least some of the lower percentage or count values). In this way, the population metric combines multiple independent metrics into a single numerical value. This final single numerical value associated with the Xb population considers or represents the quality of the segmentation of each individual step in the gating process to obtain Xb along with the properties related to the Xb population data distribution.

Exemplary population metric techniques involve various ways of combining and selecting preliminary information to produce a population based metric. Aggregation operators such as, as nonlimiting examples, minimum, maximum, average, or other meaningful approaches to combine numbers into a single value are applied in some embodiments.

In some instances, embodiments of the present invention are used in a real-time analysis approach for assessing the quality of results provided by automated flow cytometry solutions. In some instances, embodiments of the present invention are used in a post analysis approach for assessing the quality of results provided by automated flow cytometry solutions In some instances, embodiments of the present invention are used to assess the quality of results provided for individual tubes or testing containers. Hence, where a measurement is incorrect for multiple tubes but consistent across those tubes, in some embodiments the quality is determined to be unacceptable. Further, embodiments of the present invention encompass multi-tube analysis techniques that do not involve or require shared markers among the tubes. Relatedly, the quality control assessments as disclosed herein are applied to single tube kits in some embodiments. Accordingly, certain embodiments of the present invention are used to determine the certainty or uncertainty related to a single tube run. In some cases, metrics are exported into a Laboratory Information System (LIS) as input for decision making rules.

Based on the above, embodiments of the present invention are seen to encompass techniques which are used in a variety of systems and methods for characterizing cells or particles, including for example flow cytometers. Embodiments encompass the use of automated gating to obtain cellular or particle characterization results (e.g. histograms), as well as automated validation techniques or quality assessment analysis of the gating results. In some embodiments, validation is performed in an automated real-time manner for quality assessment analysis. In some embodiments, validation is performed in an automated off-line, post-run quality assessment analysis. Relatedly, some embodiments of the present invention encompass automated approaches which are used for validating (e.g. quality assessment) or analyzing the gating or results obtained in a histogram. In some embodiments, automated histogram-based metric or scoring is based on a single, one-dimensional, or multi-dimensional histogram. As a nonlimiting example, a region separability metric (e.g. cluster validity measure) is used in some embodiments to analyze data along a boundary line of a region for a histogram. In certain embodiments, a region separability metric is based on the use of a region boundary line that divides a 2D histogram into two separate regions. In some embodiments, a region separability metric is based on a count involving the number of events on the region boundary line. In some embodiments, a region separability metric correlates the number of events on a region boundary line with a certainty or an uncertainty related to the boundary line placement. A region separability metric includes in some embodiments the number of events on a region boundary line as a fraction or a percentage. In some embodiments, a metric transforms such a fraction or percentage of the boundary line events into a single numerical value. In some embodiments, the metric is based on a predefined limit or threshold, which allows customization of the metric. In certain embodiments, a region separability metric includes a dynamic predefined limit, that in some embodiments is changed according to either the size, or the known clinical significance, of the population being considered.

Similarly, based on the above, some embodiments encompass the use of a data distribution (e.g. similarity) metric, which is used in certain embodiments to analyze the behavior of the data within a region. In some embodiments, a data distribution metric quantifies the similarity of a population data distribution to a known theoretical distribution. In some embodiments, a data distribution metric requires a low computation load. In some embodiments, a data distribution metric uses a set of multidimensional events belonging to the same population. In some embodiments, a data distribution metric involves the calculation of sample statistics, such as mean, standard deviation, or the like, for selected dimensions. In some embodiments, a data distribution metric is based on a sample data distribution that is normalized. In some embodiments, a data distribution metric is based on sample statistics that are used to construct an ideal theoretical distribution using a predefined model. In some embodiments, an ideal theoretical distribution is normalized, as a nonlimiting example the distribution is normalized as a Gaussian curve in some embodiments. According to some embodiments, a data distribution metric is based on the calculation of a similarity measure, such as a correlation coefficient, an absolute error, a sum or paired event differences, or the like, where the similarity measure compares the theoretical model against the sample distribution. In some embodiments, a data distribution metric is based on the calculation of a data distribution score in a selected multi-dimensional space. In some embodiments, a data distribution metric is based on the calculation of a data distribution score calculated in each dimension, where an aggregator operator (e.g. average, minimum, or the like) is used to combine each individual result into a final result. In some embodiments, a data distribution score is based on an algorithm equation or relationship that includes a weighted metric term and an original metric term. In some embodiments, a data distribution score is based on an algorithm equation or relationship that includes a population significance term. According to some embodiments, a population significance term includes a mathematical expression or relationship that captures a population percent and/or fraction, and a significance threshold of the population percent and/or fraction. In some embodiments, a population significance term includes a mathematical expression or relationship that captures a population number of events, and a significance threshold of the population number of events.

Further, based on the above, some embodiments of the present invention encompass systems and methods for automated population based metrics and scoring techniques. In some embodiments, such metrics or scoring techniques are generated for individual populations of interest. In some embodiments, population based metrics are based on gating sequences, histogram based metrics and their statistical significance, and aggregation operators, to produce a single numerical value. In certain embodiments an automated population based metric operates to summarize sample results and/or improve the efficiency of reviewing sample results. As a nonlimiting example, the automated population based metric simplifies or streamlines a laboratory work flow. In some embodiments, a population based metric combines independent metrics using logic or aggregator operators, as a nonlimiting example a minimum value, to yield a single numerical value. In some embodiments, an automated population based metric is transformed into a weighted or qualified metric by applying a transformation function, thereby allowing control over the impact of individual independent metrics on factors such as the summary of sample results and/or the efficiency of reviewing sample results (e.g. work flow). In some embodiments a transformation technique or algorithm equation involves a weight factor term (e.g. alpha) to control the rate of change of the original metric (e.g. M). In certain embodiments, a transformation technique or algorithm equation includes a maximum (or minimum) metric value term (e.g. beta=100). In some embodiments, a transform technique or algorithm equation includes a population significance term that captures the relative importance of the population expressed as a percent (or fraction), a number of events, or as a statistic. In some embodiments, it also includes a qualitative heuristic assessment number. In certain embodiments a population significance term includes a mathematical expression or relationship capturing a population percent or fraction and a significance threshold of the population percent or fraction.

In some embodiments, a population significance term includes a mathematical expression or relationship capturing a population number of events and a significance threshold of the population number of events.

Figure 8:
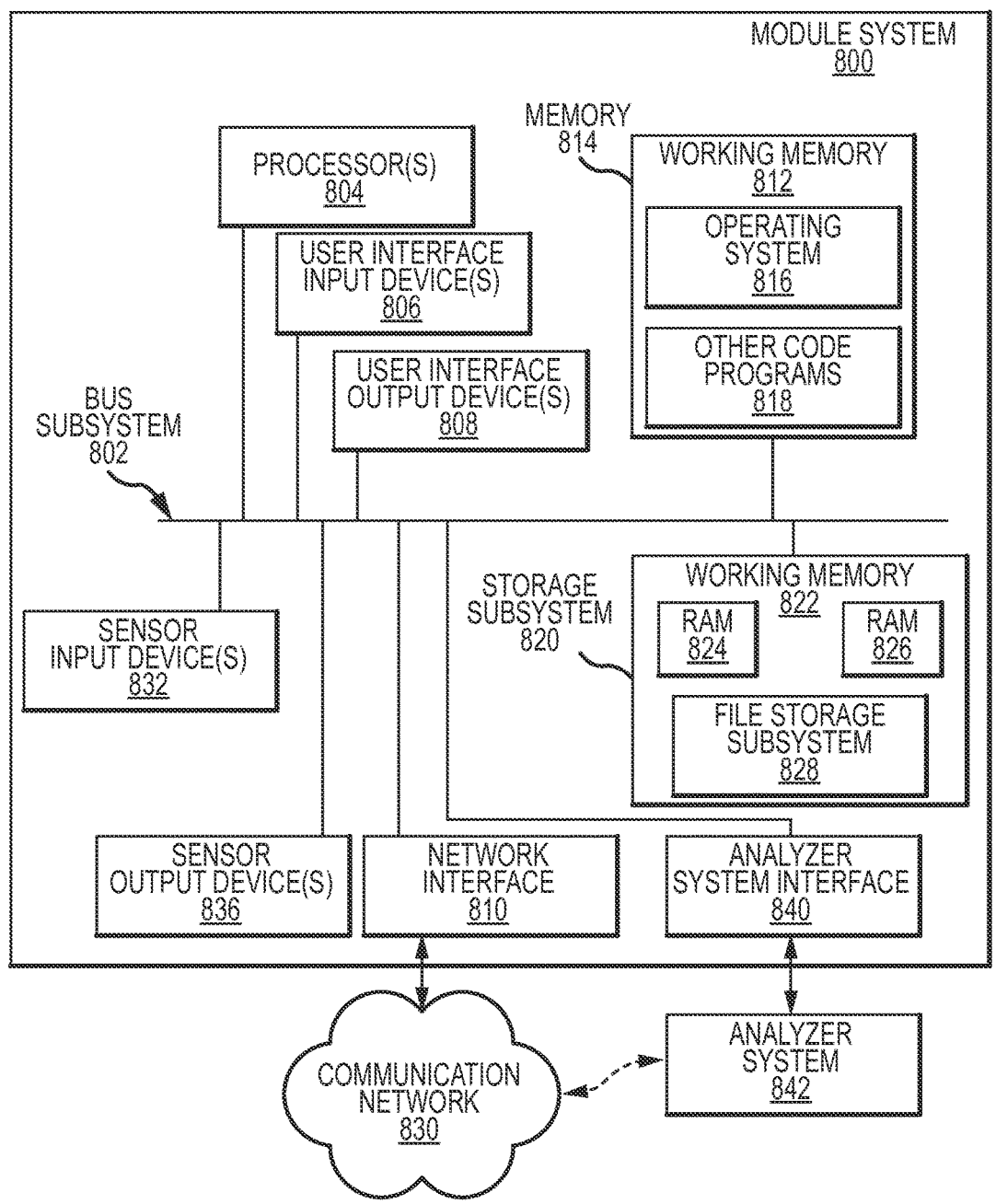
FIG. 8 depicts aspects of a module or modules that can be implemented in association with a cellular analysis or flow cytometry system, according to embodiments of the present invention.

FIG. 8 is a simplified block diagram of an exemplary module system that broadly illustrates how individual system elements for a module system 800 may be implemented in a separated or more integrated manner. Module system 800 may be part of or in connectivity with a cellular analysis or flow cytometry system for detecting and quantifying various sample particles and related populations of interest within the sample particles, and/or may be part of or in connectivity with an evaluation system for assessing the quality of a boundary or segmentation used for isolating a subset of events from a set of accumulated events, where the subset corresponds to a population of interest sharing a physical property and the set corresponds to sample particles. Systems implementing Beckman Coulter tetraCXP system software, stemCXP and CytoDiff CXP software are nonlimiting examples of such flow cytometers. Module system 800 is well suited for producing data or receiving input related to a flow cytometry analysis. In some instances, module system 800 includes hardware elements that are electrically coupled via a bus subsystem 802, including one or more processors 804, one or more input devices 806 such as user interface input devices, and/or one or more output devices 808 such as user interface output devices. In some instances, system 800 includes a network interface 810, and/or an analyzer system interface 840 that can receive signals from and/or transmit signals to an analyzer system 842. In some instances, system 800 includes software elements, for example shown here as being currently located within a working memory 812 of a memory 814, an operating system 816, and/or other code 818, such as a program configured to implement one or more aspects of the techniques disclosed herein.

In some embodiments, module system 800 may include a storage subsystem 820 that can store the basic programming and data constructs that provide the functionality of the various techniques disclosed herein. For example, software modules implementing the functionality of method aspects, as described herein, may be stored in storage subsystem 820. These software modules may be executed by the one or more processors 804. In a distributed environment, the software modules may be stored on a plurality of computer systems and executed by processors of the plurality of computer systems. Storage subsystem 820 can include memory subsystem 822 and file storage subsystem 828. Memory subsystem 822 may include a number of memories including a main random access memory (RAM) 826 for storage of instructions and data during program execution and a read only memory (ROM) 824 in which fixed instructions are stored. File storage subsystem 828 can provide persistent (non-volatile) storage for program and data files, and may include tangible storage media which may optionally embody patient, treatment, assessment, or other data. File storage subsystem 828 may include a hard disk drive, a floppy disk drive along with associated removable media, a Compact Digital Read Only Memory (CD-ROM) drive, an optical drive, DVD, CD-R, CD RW, solid-state removable memory, other removable media cartridges or disks, and the like. One or more of the drives may be located at remote locations on other connected computers at other sites coupled to module system 800. In some instances, systems may include a computer-readable storage medium or other tangible storage medium that stores one or more sequences of instructions which, when executed by one or more processors, can cause the one or more processors to perform any aspect of the techniques or methods disclosed herein. One or more modules implementing the functionality of the techniques disclosed herein may be stored by file storage subsystem 828. In some embodiments, the software or code will provide protocol to allow the module system 800 to communicate with communication network 830. Optionally, such communications may include dial-up or internet connection communications.

It is appreciated that system 800 can be configured to carry out various aspects of methods of the present invention. For example, processor component or module 804 can be a microprocessor control module configured to receive cellular parameter signals from a sensor input device or module 832, from a user interface input device or module 806, and/or from an analyzer system 842, optionally via an analyzer system interface 840 and/or a network interface 810 and a communication network 830. In some instances, sensor input device(s) may include or be part of a cellular analysis system such as a flow cytometer. In some instances, user interface input device(s) 806 and/or network interface 810 may be configured to receive cellular parameter signals generated by a cellular analysis system such as a flow cytometer. In some instances, analyzer system 842 may include or be part of a cellular analysis system such as a flow cytometer.

Processor component or module 804 can also be configured to transmit cellular parameter signals, optionally processed according to any of the techniques disclosed herein, to sensor output device or module 836, to user interface output device or module 608, to network interface device or module 810, to analyzer system interface 840, or any combination thereof. Each of the devices or modules according to embodiments of the present invention can include one or more software modules on a computer readable medium that is processed by a processor, or hardware modules, or any combination thereof. Any of a variety of commonly used platforms, such as Windows, Macintosh, and Unix, along with any of a variety of commonly used programming languages, may be used to implement embodiments of the present invention.

User interface input devices 806 may include, for example, a touchpad, a keyboard, pointing devices such as a mouse, a trackball, a graphics tablet, a scanner, a joystick, a touchscreen incorporated into a display, audio input devices such as voice recognition systems, microphones, and other types of input devices. User input devices 806 may also download a computer executable code from a tangible storage media or from communication network 830, the code embodying any of the methods or aspects thereof disclosed herein. It will be appreciated that terminal software may be updated from time to time and downloaded to the terminal as appropriate. In general, use of the term "input device" is intended to include a variety of conventional and proprietary devices and ways to input information into module system 800.

User interface output devices 806 may include, for example, a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from module system 800 to a user.

Bus subsystem 802 provides a mechanism for letting the various components and subsystems of module system 800 communicate with each other as intended or desired. The various subsystems and components of module system 800 need not be at the same physical location but may be distributed at various locations within a distributed network. Although bus subsystem 802 is shown schematically as a single bus, alternate embodiments of the bus subsystem may utilize multiple busses.

Network interface 810 can provide an interface to an outside network 830 or other devices. Outside communication network 830 can be configured to effect communications as needed or desired with other parties. It can thus receive an electronic packet from module system 800 and transmit any information as needed or desired back to module system 800. As depicted here, communication network 830 and/or analyzer system interface 840 may transmit information to or receive information from an analyzer system 842 such as a flow cytometer.

In addition to providing such infrastructure communications links internal to the system, the communications network system 830 may also provide a connection to other networks such as the internet and may comprise a wired, wireless, modem, and/or other type of interfacing connection.

It will be apparent to the skilled artisan that substantial variations may be used in accordance with specific requirements. For example, customized hardware might also be used and/or particular elements might be implemented in hardware, software (including portable software, such as applets), or both. Further, connection to other computing devices such as network input/output devices may be employed. Module terminal system 800 itself can be of varying types including a computer terminal, a personal computer, a portable computer, a workstation, a network computer, or any other data processing system. Due to the ever-changing nature of computers and networks, the description of module system 800 depicted in FIG. 8 is intended only as a specific example for purposes of illustrating one or more embodiments of the present invention. Many other configurations of module system 800 are possible having more or less components than the module system depicted in FIG. 8. Any of the modules or components of module system 800, or any combinations of such modules or components, can be coupled with, or integrated into, or otherwise configured to be in connectivity with, any of the cellular or particle analysis system embodiments disclosed herein. Relatedly, any of the hardware and software components discussed above can be integrated with or configured to interface with other medical assessment or treatment systems used at other locations.

In some embodiments, the module system 800 can be configured to receive one or more particle analysis parameters of a patient at an input module. The particle analysis parameters can relate to or include a subset of events from a set of accumulated events, where the subset corresponds to a population of interest sharing a physical property and the set corresponds to sample particles. The particle analysis parameters can also relate to or include information relating to a boundary used for isolating a subset of events from a set of accumulated events. In some cases, the module system 800 can determine a quality assessment metric for such a boundary, using a module of the system 800. Optionally, certain aspects of the analysis can be determined by an output device, and transmitted to an analysis system or a sub-device of an analysis system. Any of a variety of data related to sample particles or populations of interest, or to boundaries or other segmenting features used to isolate or define populations of interest, can be input into the module system.

Relatedly, in some instances a system includes a processor configured to receive particle analysis data as input. Optionally, a processor, storage medium, or both, may be incorporated within a particle or cellular analysis machine, such as a flow cytometer. In some instances, the analysis machine may generate particle analysis data or other information for input into the processor. In some instances, a processor, a storage medium, or both, can be incorporated within a computer, and the computer can be in communication with a particle analysis machine. In some instances, a processor, a storage medium, or both, can be incorporated within a computer, and the computer can be in remote communication with a particle analysis machine via a network.

Embodiments of the present invention encompass systems and methods for evaluating the results of flow cytometry data segmentation techniques. Exemplary systems may be configured to receive as input a boundary or other segmentation feature that operates to isolate a subset of events from a set of accumulated events. Systems can also be configured to determine a quality assessment metric for the boundary, and output or display information that provides an indication of the quality assessment metric.

Exemplary systems and methods for evaluating segmentation results related to analysis of sample particles, for example biological particles of a sample obtained from an individual, can include obtaining or receiving a plot of a set of accumulated events, where a boundary isolates a subset of events from other events of a set of accumulated events, and outputting a quality assessment metric for the boundary. In some cases, a particle analysis system such as a flow cytometer may include a conduit configured to receive and direct movement of the biological sample thorough an aperture, and a measuring device to collect data concerning the biological sample. The system can be configured to process the data to obtain a quality assessment metric for a boundary associated with the data. In some cases, a particle analysis system may include a mechanism for obtaining data for a biological sample as it passes through a conduit or aperture, a processor, and a storage medium having a computer application that, when executed by the processor, is configured to cause the system to use the data to determine a quality assessment metric for a boundary or segmentation technique associated with the data. The system can also be configured to output from the processor information relating to the quality assessment metric for the boundary or segmentation technique. In some cases, a particle analysis system can include a processor, and a storage medium having a computer application that, when executed by the processor, is configured to cause the system to access a plot of a set of accumulated events, where the set of accumulated events includes the subset of events, to isolate, with a boundary, the subset of events from other events of the set of accumulated events, and to determining a quality assessment metric for the boundary. In some cases, the processor can be configured to cause the system to output information relating to the quality assessment metric. In some cases, a particle analyzer machine or flow cytometer can generate the subset of events and the set of accumulated events. In some cases, a flow cytometer can be in remote communication with a system that determines a quality assessment metric for a boundary. In some cases, the remote communication can be by way of a network.

Figure 9:
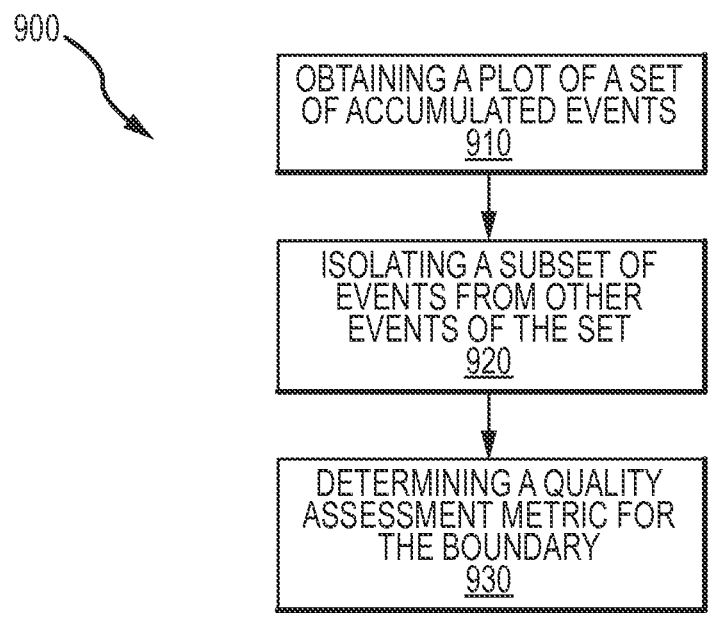
FIG. 9 depicts aspects of a method for determining a quality assessment metric for a boundary, according to embodiments of the present invention.

As shown in FIG. 9, an exemplary method 900 for assessing the quality of a boundary or data segmentation result can include obtaining a plot of a set of accumulated events, as indicated by step 910. The method can also include isolating a subset of events from other events of the set, as indicated by step 920. The set of accumulated events shown at step 910 can include the subset of events shown at step 920. The isolating step can be performed using a boundary or other means for separation. Further, the method may include determining a quality assessment metric for the boundary, as indicated by step 930.

Figure 10:
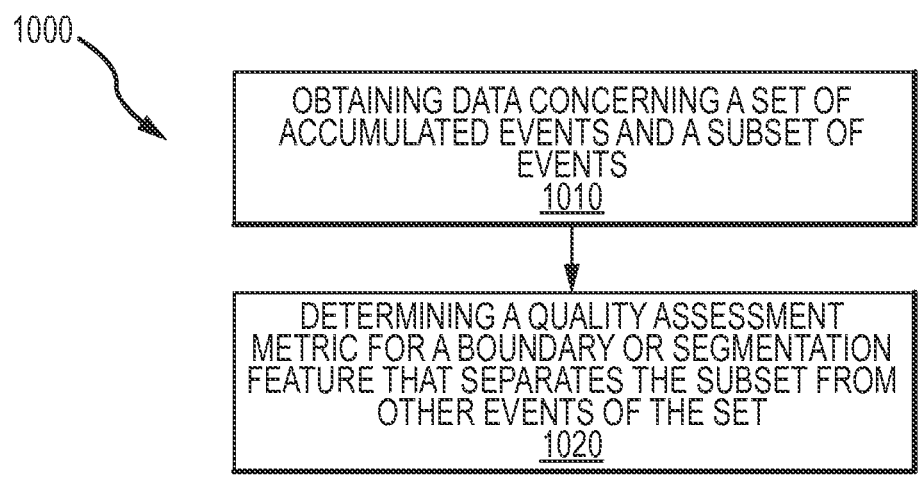
FIG. 10 depicts aspects of a method for determining a quality assessment metric for a boundary or segmentation feature that separates a subset of events from other events of a set, according to embodiments of the present invention.

As shown in FIG. 10, an exemplary method 1000 for assessing the quality of a boundary of data segmentation feature can include obtaining data concerning a set of accumulated events and a subset of events, as indicated in step 1010. The method can also include determining a quality assessment metric for a boundary or data segmentation feature which separates the subset of events from other events of the set, as indicated by step 1020.

Figure 11:
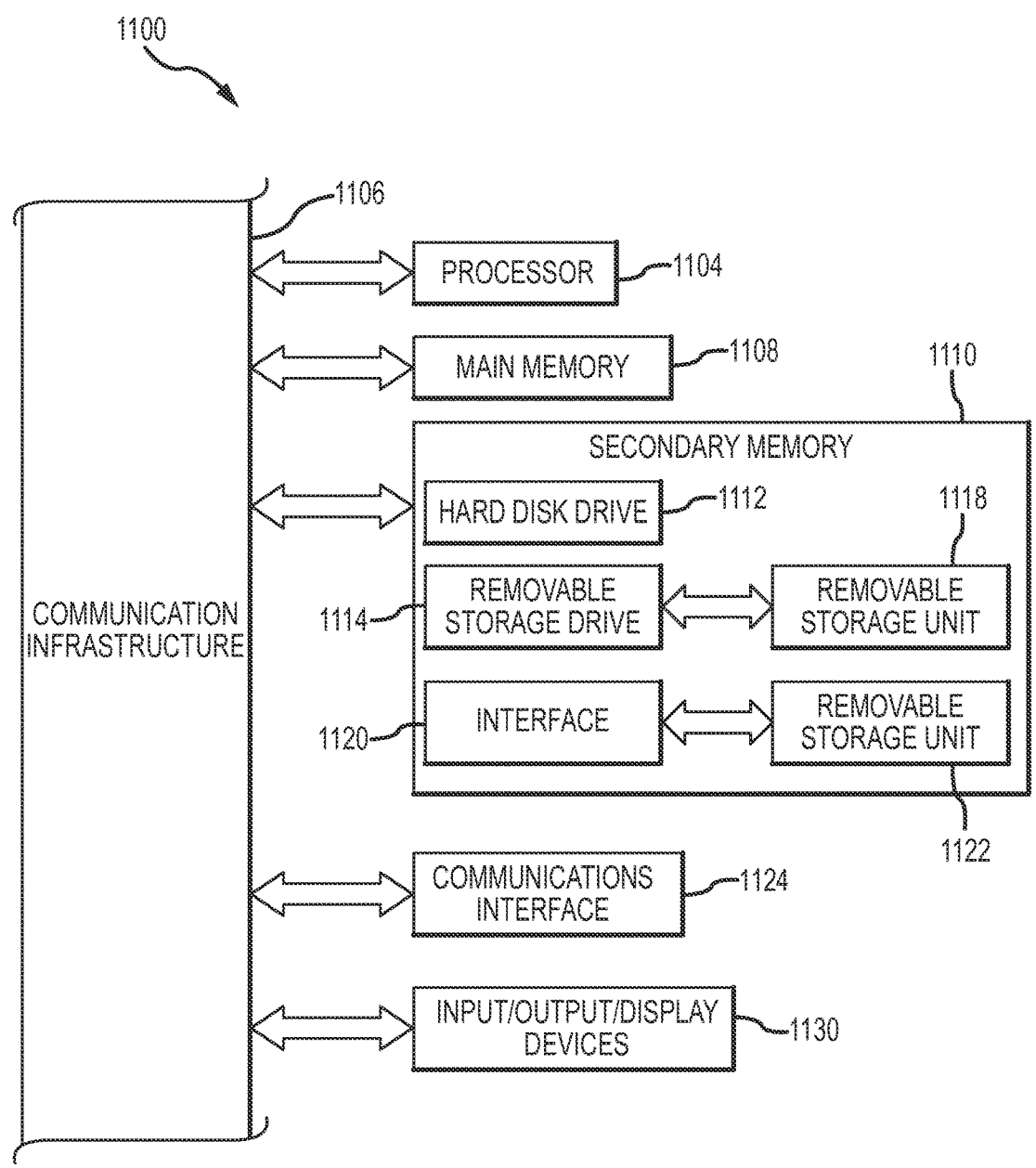
FIG. 11 depicts aspects of a computer system, according to embodiments of the present invention.

In some embodiments, a particle analysis system and its components can be implemented using hardware, firmware, software or a combination thereof and can be implemented in a computing device such as a computer system. In an embodiment, an exemplary computer system 1100, is shown in FIG. 11. Computer system 1100 includes one or more processors, such as processor 1104. Processor 1104 is connected to a communication infrastructure 1106 (such as a bus).

Computer system 1100 also includes a main memory 1108, for example a random access memory (RAM), and can also include a secondary memory 1110. Secondary memory 1110 can include, for example, a hard disk drive 1112 and/or a removable storage drive 1114, representing a floppy disk drive, an optical disk drive, or the like. Removable storage drive 1114 reads from and/or writes to a removable storage unit 1118 in a well-known manner. Removable storage unit 1118, represents a floppy disk, optical disk, memory card, or the like, which is read by and written to by removable storage drive 1114. As will be appreciated, the removable storage unit 1118 includes a computer usable storage medium having stored therein computer software and/or data.

In alternative embodiments, secondary memory 1110 can include other similar means, such as a removable storage unit 1122 and an interface 1120, for allowing computer programs or other instructions to be loaded into computer system 1100. Examples of such can include a program cartridge and cartridge interface (such as that found in video game devices), a removable memory chip (such as an EPROM, or PROM) and associated socket, and other removable storage units and interfaces.

Computer system 1100 can also include a communication interface 1124. Communication interface 1124 enables computer 1100 to communicate with external and/or remote devices. Examples of communications interface 1124 can include a modem, a network interface (such as an Ethernet card), a communications port, a PCMCIA slot and card, or the like. Computer system 1100 receives data and/or computer program products via communication network 1124. Software and data can be transferred via communications interface 1124.

Computer programs (also called computer control logic) are stored in main memory 1108 and/or secondary memory 1110. Computer programs can also be received via communications interface 1124 and/or signals. Such computer programs, when executed, enable computer system 1100 to perform the features of the present invention as discussed herein. In particular, the computer programs, when executed, enable processor 1104 to perform the features of embodiments of the present invention. Accordingly, such computer programs represent controllers of computer system 1100.

In an embodiment where the invention is implemented using software, the software can be stored in a computer program product having a tangible computer readable medium and loaded into computer system 1100 using removable storage drive 1114, hard disk drive 1112 or communications interface 1124. The control logic (software), when executed by processor 1104, causes processor 1104 to perform the functions of embodiments of the invention as described herein.

Computer 1100 also includes input/output/display devices 1130, such as one or more monitors, keyboards, pointing devices, and the like.

Each of the calculations or operations described herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

All patents, patent publications, patent applications, journal articles, books, technical references, and the like discussed in the instant disclosure are incorporated herein by reference in their entirety for all purposes.

It is to be understood that the figures and descriptions of the invention have been simplified to illustrate elements that are relevant for a clear understanding of the invention. It should be appreciated that the figures are presented for illustrative purposes and not as construction drawings. Omitted details and modifications or alternative embodiments are within the purview of persons of ordinary skill in the art.

It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

What is claimed is:

1. A method of assessing the reliability of a result generated by a flow cytometer and providing a warning of questionable results, the method comprising:
   processing, on a flow cytometer, a plot of a set of accumulated events, wherein the set of accumulated events includes a subset of events from the set of accumulated events, the subset corresponding to a population of interest sharing a physical property and the set corresponding to sample particles;
   isolating, with a boundary, the subset of events from other events of the set of accumulated events;
   determining a quality assessment metric for the boundary, wherein the quality assessment metric is indicative of the reliability of the result generated by the flow cytometer;
   identifying questionable flow cytometry results based on the quality assessment metric, wherein questionable results are caused by at least one of a hardware malfunction, an incorrect instrument setting, improper preparation of the sample, excessive aging of the sample, or a highly abnormal sample; and
   wherein the flow cytometer provides a warning of the questionable results.

2. The method according to claim 1, wherein the result comprises a determination of the number of sample particles making up the population of interest.

3. The method according to claim 2, wherein placement of the boundary is automated.

4. The method according to claim 2, wherein placement of the boundary is performed manually.

5. The method according to claim 2, wherein the quality assessment metric is based on a distance between the subset of events and the boundary.

6. The method according to claim 2, wherein the quality assessment metric is based on a distance between the subset of events and a characteristic point.

7. The method according to claim 6, wherein the characteristic point comprises a member selected from the group consisting of a mean of the subset and a mode of the subset.

8. The method according to claim 2, wherein the quality assessment metric is based on a number of events falling on the boundary.

9. The method according to claim 2, wherein the boundary at least partially defines a region corresponding to the population of interest.

10. The method according to claim 2, wherein the quality assessment metric is based on a comparison between a statistical parameter calculated for the subset and a theoretical distribution.

11. The method according to claim 10, wherein the statistical parameter is a mean or a standard deviation.

12. The method according to claim 10, wherein the theoretical distribution is a Gaussian distribution.

13. The method according to claim 10, wherein the comparison is based on a similarity measure characterizing the statistical parameter and the theoretical distribution, and wherein the similarity measure is calculated based on a sum of paired event distances or a correlation coefficient.

14. The method according to claim 2, wherein the quality assessment metric is a function of a combination of multiple independent metrics, the combination of multiple independent metrics comprising a first independent metric and a second independent metric.

15. The method according to claim 14, wherein the first independent metric and the second independent metric are combined using an aggregation operator.

16. The method according to claim 15, wherein the aggregation operator comprises a member selected from the group consisting of an average, a minimum, and a maximum.

17. The method according to claim 14, wherein the first independent metric is based on a number of events falling on the boundary and the second independent metric is based on a comparison between a statistical parameter calculated for the subset and a theoretical distribution.

18. The method according to claim 14, wherein the first independent metric corresponds to the population of interest, and the second independent metric corresponds to another population of interest.

19. A method of assessing the quality of data generated by a flow cytometer for a subset of a set of accumulated events and providing a warning of questionable results, the method comprising:
   generating data for the set of accumulated events, wherein the set of accumulated events corresponds to sample particles;
   segmenting, using a data segmentation technique, data for the subset of the set of accumulated events, wherein the subset corresponds to a population of interest
   determining a quality assessment metric for the data segmentation technique;
   determining the quality of the data for the subset based on the quality assessment metric;
   identifying questionable flow cytometry results based on the quality assessment metric, wherein questionable results are caused by at least one of a hardware malfunction, an incorrect instrument setting, improper preparation of the sample, excessive aging of the sample, or a highly abnormal sample; and
   wherein the flow cytometer provides a warning of the questionable results.

20. A flow cytometer, comprising:
   an electronic detection apparatus configured to generate data for sample particles, wherein the data corresponds to a set of accumulated events, and wherein the set of accumulated events includes a subset of events corresponding to a population of interest sharing a physical property;
   a display configured to display a plot of the set of accumulated events and a boundary that isolates the subset of events from other events of the set of accumulated events;
   a processor;
   a control logic executed by the processor to determine a quality assessment metric for the boundary, wherein the quality assessment metric is indicative of the reliability of the data generated for the sample particles; wherein, if questionable results are obtained based on the quality assessment metric, wherein questionable results are caused by at least one of a hardware malfunction, an incorrect instrument setting, improper preparation of the sample, excessive aging of the sample, or a highly abnormal sample, a warning system that provides a warning of the questionable results.

21. The method according to claim 1, wherein the quality assessment metric is a numerical value between a lower limit and an upper limit, wherein a numerical value at or closer to the lower limit indicates a low reliability of the result, wherein a numerical value at or closer to the upper limit indicates a high reliability of the result.

22. The method according to claim 21, wherein a low reliability indicates one or all of (i) low quality of the underlying data or sample, (ii) a flow cytometer malfunction, or (iii) an improperly drawn boundary.

23. The method according to claim 21, wherein the quality assessment metric is based on a number of events falling on the boundary, wherein the number of events on the boundary is divided by the total number of events analyzed in order to determine a percent of events on the boundary, wherein the percent of events on the boundary is divided by a threshold value comprising the numerical valve between an upper limit and a lower limit.

* * * * *